US012535084B2

(12) United States Patent
Ishikawa

(10) Patent No.: US 12,535,084 B2
(45) Date of Patent: Jan. 27, 2026

(54) COVER BOARD ATTACHABLE TO CEILING FAN

(71) Applicant: ISHIKAWA CO., LTD., Niigata (JP)

(72) Inventor: Sachio Ishikawa, Niigata (JP)

(73) Assignee: ISHIKAWA CO., LTD., Niigata (JP)

( * ) Notice: Subject to any disclaimer, the term of this patent is extended or adjusted under 35 U.S.C. 154(b) by 0 days.

(21) Appl. No.: 19/066,111

(22) Filed: Feb. 27, 2025

(65) Prior Publication Data

US 2025/0290523 A1 Sep. 18, 2025

(30) Foreign Application Priority Data

Mar. 12, 2024 (JP) ................................ 2024-037790
Jan. 14, 2025 (JP) ................................ 2025-004965

(51) Int. Cl.
*F04D 29/54* (2006.01)
*A61L 9/20* (2006.01)
*F04D 25/08* (2006.01)

(52) U.S. Cl.
CPC ............ *F04D 29/541* (2013.01); *A61L 9/205* (2013.01); *F04D 25/088* (2013.01)

(58) Field of Classification Search
CPC .... F04D 25/088; F04D 29/541; F04D 29/444; F04D 29/542; F04D 29/544; F04D 29/545; A61L 9/205
See application file for complete search history.

(56) References Cited

U.S. PATENT DOCUMENTS

| | | | | |
|---|---|---|---|---|
| 2,378,012 A * | 6/1945 | Herbster | ................. | F24F 7/013 454/310 |
| 5,513,953 A * | 5/1996 | Hansen | ...................... | F24F 7/10 415/213.1 |
| 8,087,878 B2 * | 1/2012 | Chen | ...................... | F04D 29/442 62/263 |
| 9,702,576 B2 * | 7/2017 | Avedon | ................... | F24F 7/007 |
| 9,719,525 B2 * | 8/2017 | Cunnane | ............... | F04D 29/441 |
| 2006/0128299 A1 * | 6/2006 | Wu | ......................... | F24F 7/007 454/230 |

FOREIGN PATENT DOCUMENTS

| | | | | |
|---|---|---|---|---|
| JP | 3080670 U | 10/2001 | | |
| WO | WO-2021237197 A1 * | 11/2021 | ............... | A61L 9/22 |

* cited by examiner

*Primary Examiner* — Nathaniel E Wiehe
*Assistant Examiner* — Jason G Davis
(74) *Attorney, Agent, or Firm* — HAUPTMAN HAM, LLP

(57) ABSTRACT

A cover board attachable to a ceiling fan, which is capable of increasing air circulation efficiency with the ceiling fan and raising the temperature of a wall surface inside a room is provided. A cover board attachable to a ceiling fan includes a base board body for covering a ceiling inside a room, a mounting hole provided on the center of the base board body, through which the ceiling fan is to be inserted, and a plurality of flow guide plates arranged radially on the base board body from an outer area of an outer circumference of the mounting hole toward an outer edge of the base board body. The base board body and the flow guide plates are provided with photocatalyst, respectively, which is sprayed onto surfaces thereof.

6 Claims, 4 Drawing Sheets

COVER BOARD ATTACHABLE TO CEILING FAN

RELATED APPLICATIONS

The present application is based on and claims priority from Japanese Patent application numbers JP 2024-037790 filed on Mar. 12, 2024 and JP 2025-004965 filed on Jan. 14, 2025, the entire contents of which are incorporated herein by reference in their entirety.

TECHNICAL FIELD

The present invention relates to a cover board attachable to a ceiling fan, in particular, belongs to the technical field of a cover board for increasing air circulation efficiency with a ceiling fan and raising the temperature of a wall surface inside a room.

BACKGROUND ART

In a conventional ceiling fan illuminating device proposed in Patent Literature 1, as described "in a ceiling fan device to be mounted for use on a ceiling portion inside a room, fans that rotate for moving air upward and downward or agitating air inside a room, which are arranged to form a radial pattern from the center, and which have titanium oxide applied or adhered to the surfaces thereof for cleaning the air, for example, to deodorize the air or decompose organic compounds" (see claim 1 of Patent Literature 1), a surface layer with a titanium oxide coating film, which exhibits photocatalytic effects, is formed on each of the surfaces of the ceiling fans.

CITATION LIST

Patent Literature

[Patent Literature 1] JP-U-3080670

SUMMARY OF INVENTION

Technical Problem

The temperature inside a room is affected by the surface temperature of a wall surface, the surface temperature of a window glass, and the temperature of a window frame. The temperature of the air inside a room tends to be higher than the surface temperature of the wall surfaces and the like, however, for example, if the surface temperature of an exterior wall, the surface temperature of the window glass, or the like becomes too low, the air which is contact with that portion would be cooled and thus the temperature would drop throughout the room. The air that has been cooled moves from the top to bottom, which may cause the formation of condensation. Accordingly, it is important to raise the temperature of the wall surfaces inside the room.

However, in the ceiling fan illuminating device according to Patent Literature 1, although the ceiling fans circulate the air, the warm air near the ceiling does not sufficiently reach the wall surfaces inside the room. Thus, the temperature of the wall surface inside the room cannot be raised, and this has been a problem to be solved.

Therefore, the present invention has been made in view of the circumstances described above, and an object thereof is to provide a cover board attachable to a ceiling fan, which is capable of increasing air circulation efficiency with the ceiling fan and raising the temperature of a wall surface inside a room.

Solution to Problem

In order to solve the problem described above, the present invention provides, as a first aspect, a cover board 1 attachable to a ceiling fan 3, comprising:

- a base board body 2 for covering a ceiling 11 inside a room 10;
- a mounting hole 4 provided on a center of the base board body 2, through which the ceiling fan 3 is to be inserted; and
- a plurality of flow guide plates 51 arranged radially on the base board body 2 from an outer area K of an outer circumference 40 of the mounting hole 4 toward an outer edge 20 of the base board body 2.

Furthermore, the present invention provides, as a second aspect, the cover board attachable to a ceiling fan according to the first aspect, wherein the base board body 2 and the flow guide plates 51 are provided with photocatalyst 32, respectively, which is sprayed onto surfaces thereof.

Still further, the present invention provides, as a third aspect, the cover board attachable to a ceiling fan according to the first aspect, further comprising a plurality of fixing flow guide plates 52 arranged on the base board body 2, which further have functions to fix the cover board 1 to the ceiling 10, wherein the fixing flow guide plates 52 are arranged to form a cross-shape, and formed to be thicker than the flow guide plates 51.

Still further, the present invention provides, as a fourth aspect, the cover board attachable to a ceiling fan according to the third aspect, wherein the base board body 2, the flow guide plates 51, and the fixing flow guide plates 52 are provided with photocatalyst 32, respectively, which is sprayed onto surfaces thereof.

Still further, the present invention provides, as a fifth aspect, the cover board attachable to a ceiling fan according to any one of the first to fourth aspect, wherein the base board body 2 is formed to have a width allowing a predetermined area of the ceiling 10 in a width direction to be covered therewith.

Advantageous Effects of Invention

According to the cover board attachable to a ceiling fan of the present invention, it is possible to increase air circulation efficiency with the ceiling fan and raise the temperature of a wall surface inside a room.

DESCRIPTION OF EMBODIMENTS

Hereinafter, a preferred embodiment of a cover board attachable to a ceiling fan according to the present invention will be described with reference to the drawings.

Figure 1:
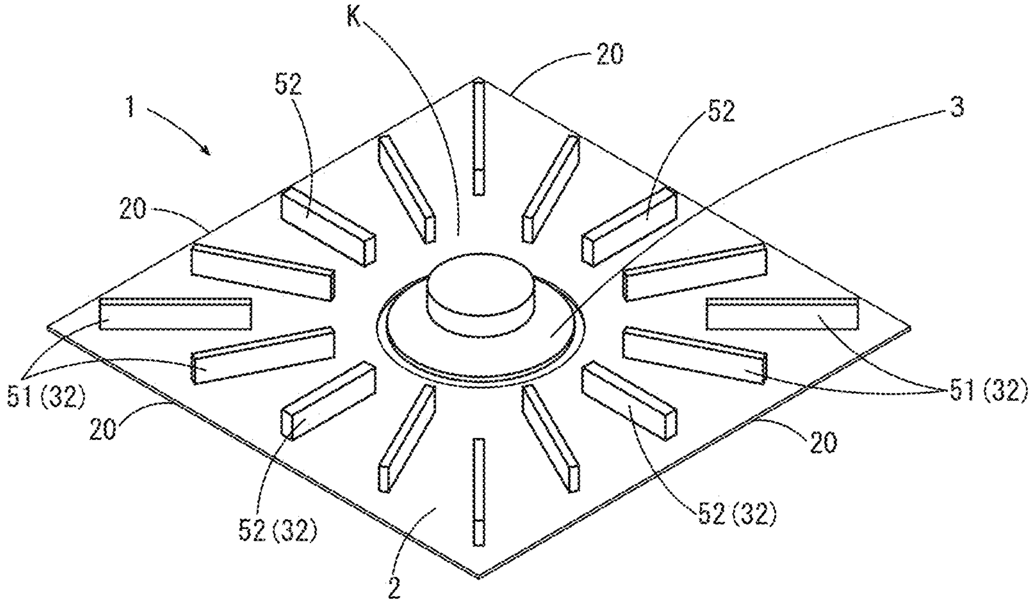
FIG. 1 is a perspective view of a cover board attachable to a ceiling fan according to the present invention.
Figure 2:
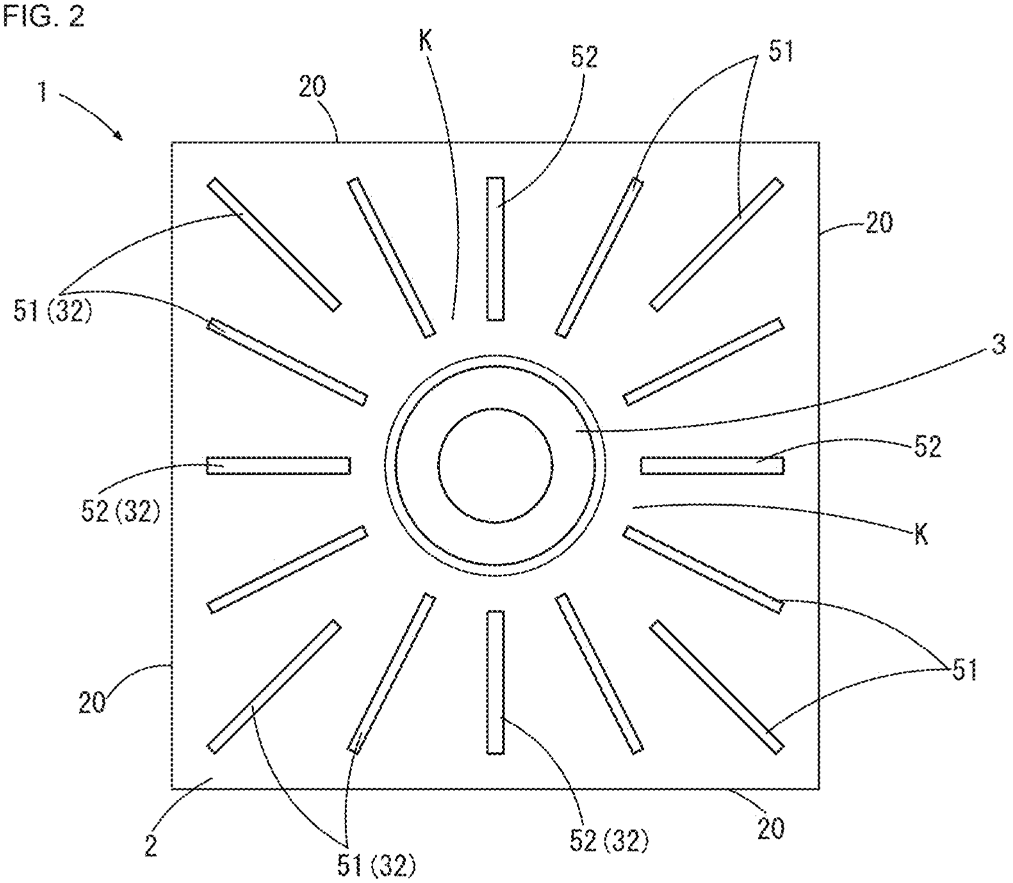
FIG. 2 is a top view of a cover board attachable to a ceiling fan.
Figure 3:
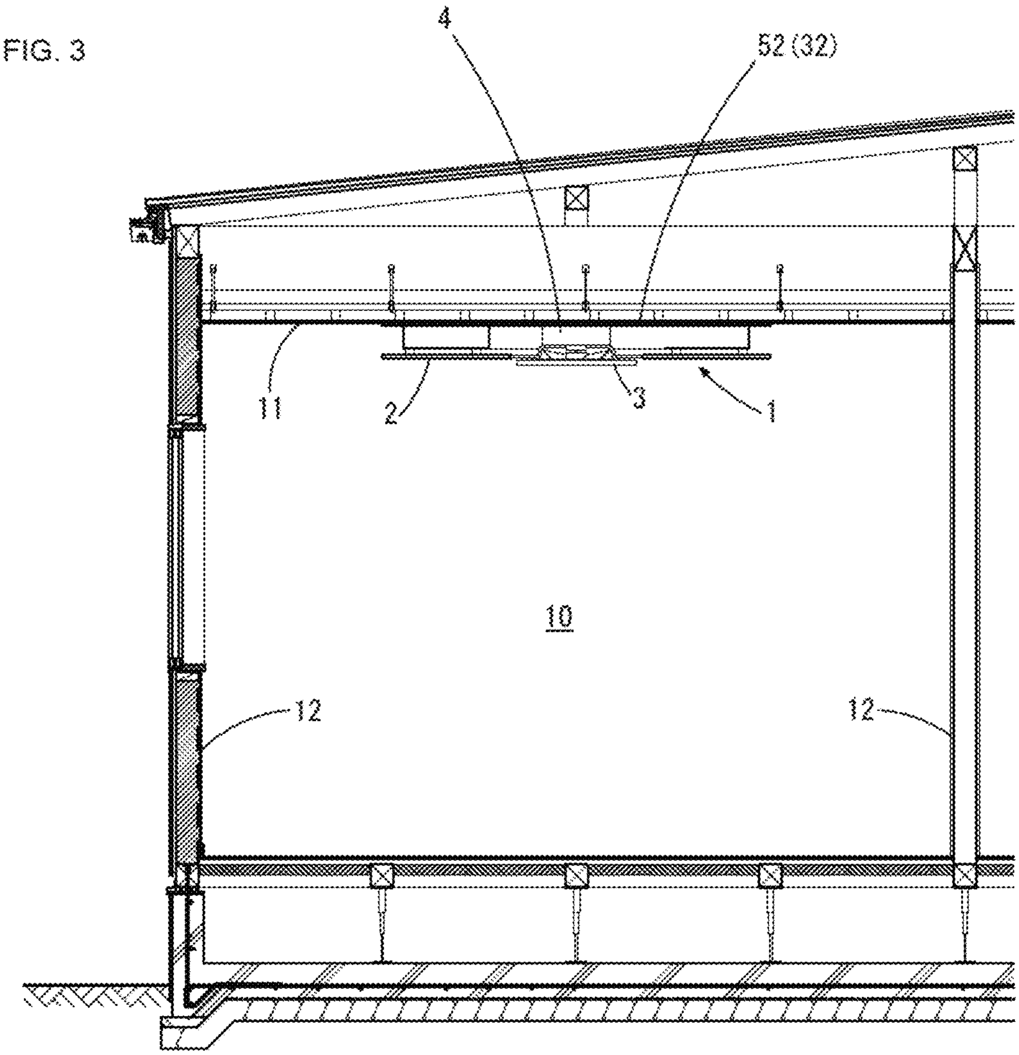
FIG. 3 is a side cross-section view in which a cover board attachable to a ceiling fan is mounted to the ceiling fan installed on a ceiling.

As illustrate in FIG. 1 to FIG. 3, a cover board 1 includes a base board body 2 having a board-shape and the size allowing a desired area of a ceiling 11 to be covered therewith, which is made of a gypsum board base finished with cloth. On the center of the base board body 2, a mounting hole 4 having a circular shape is provided such that it penetrates the base board body 2 to allow a ceiling fan 3 to be inserted therein.

On the top surface of the base board body 2, flow guide plates 51 are arranged radially from an outer area K, which is separated slightly from an outer circumference 40 of the mounting hole 4, toward an outer edge 20 of the base board body 2. Some of the flow guide plates 51 may be arranged with their distances from the center of the mounting hole 4 being different from those of the others. As illustrated in FIG. 1 and FIG. 2, the flow guide plates 51 near the four corners are arranged being spaced apart from the center of the mounting hole 4, respectively, further than the other flow guide plates 51.

For example, fixing flow guide plates 52 having functions to fix the cover board 1 to the ceiling 11 are preferably arranged to form a cross-shape. The fixing flow guide plates 52 are provided separately from the flow guide plates 51, however, not only have the functions for fixing, but also having the functions for guiding airflow in the same manner as the flow guide plates 51. The fixing flow guide plates 52 may be fixed to the ceiling 11 using adhesives, bolts, and the like, whereby the cover board 1 can be fixed to the ceiling 11. The fixing flow guide plates 52 may be formed, for example, to be thicker than the flow guide plates 51. Preferably, the flow guide plates 51 and the fixing flow guide plates 52 are formed to have rectangular parallelepiped shapes.

Thus, providing the flow guide plates 51 and the fixing flow guide plates 52 enables increase in the circulation efficiency of the air inside a room 10, and also increase in the temperature of a wall surface 12 inside the room 10. By raising the temperature of the wall surface 12, the temperature that a person inside the room 10 actually feels can be increased.

Figure 4:
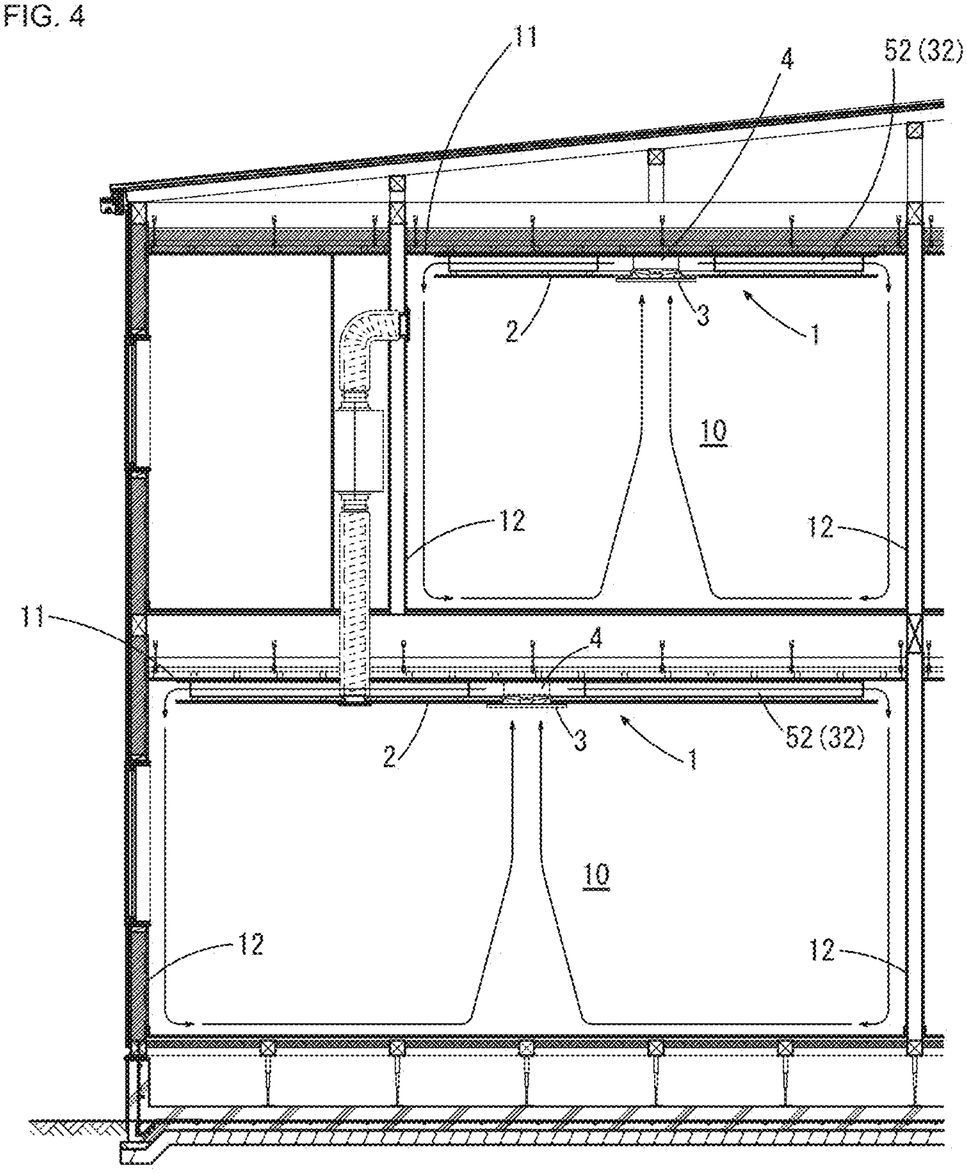
FIG. 4 is a side cross-section view in which long cover boards attachable to ceiling fans are mounted to the ceiling fans installed on ceilings of the first and second floors, respectively.

In FIG. 3, the width of the base board body 2 extends so as to cover about the half of the width of the ceiling 11, however, it is not limited thereto. For example, for adjusting the temperature of the wall surfaces further effectively, as illustrated in FIG. 4, the base board body 2 may be provided so as to cover almost the whole width of the ceiling 11. In the structure in which the base board body 2 covers almost the whole width of the ceiling 11, outlets from which the air flows downward are located close to the wall surfaces 12, and thus, as illustrated with the arrows in FIG. 4, the warm air near the ceiling 11 is easily transmitted directly to the four wall surfaces 12. In this structure, also in the case of lowering the temperature of the wall surfaces, the air is efficiently transmitted to the wall surfaces 12 so that they can be cooled easily.

Figure 5:
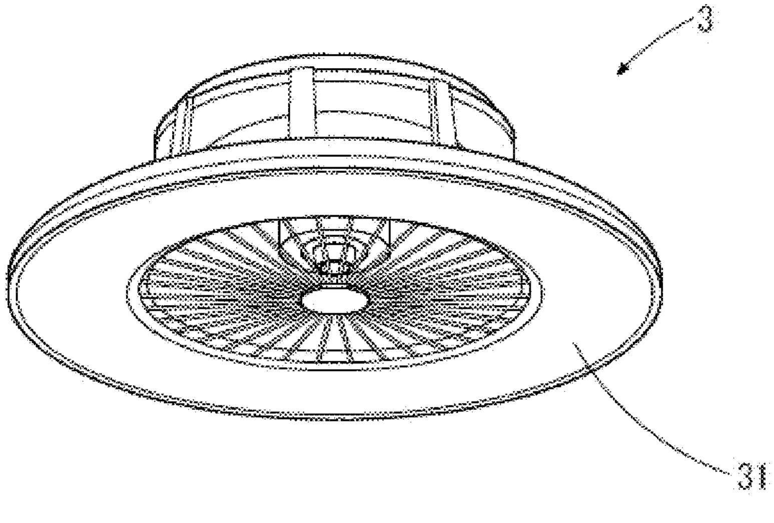
FIG. 5 is a perspective view of an example of a ceiling fan, to which a cover board attachable to the ceiling fan is to be mounted.

The ceiling fan 3 may be any fan which is commercially available. Preferably, the ceiling fan 3 may be equipped with a lighting function, such as an LED lighting 31. The ceiling fan 3 illustrated in FIG. 5 is equipped with the LED lighting 31 on its lower surface, so that the base board body 2, the flow guide plates 51, and the fixing flow guide plates 52 can be irradiated with light.

An embodiment in which photocatalyst 32 is sprayed onto the surfaces of the base board body 2, flow guide plates 51, and fixing flow guide plates 52 is preferably employed. Irradiating the base board body 2, the flow guide plates 51, and the fixing flow guide plates 52 with light from the LED lighting 31 causes the photocatalyst to function as a catalyst. Furthermore, circulation of the air by means of the ceiling fan 3 allows the air to be kept clean throughout the room.

The present invention has been described based on the embodiment referring to the drawings, however, it is not limited to the examples illustrated in the drawings but includes any design change and variations which would be made by those ordinally skilled in the art within the scope not deviating from its technical concept. For example, the shape, number, and arrangement of the flow guide plates 51 and those of the fixing flow guide plates 52 may be appropriately changed.

REFERENCE SIGNS LIST

1 cover board
2 base board body
20 outer edge
3 ceiling fan
31 LED lighting
32 photocatalyst
4 mounting hole
40 outer circumference
K outer area
51 flow guide plate
52 fixing flow guide plate
10 room
11 ceiling
12 wall surface

The invention claimed is:

1. A cover board configured to be attached to a ceiling inside a room having a ceiling fan projected downwardly from the ceiling, the cover board comprising:

a base board body configured to be disposed under the ceiling and to form a space between the base board body and the ceiling;

a mounting hole in which the ceiling fan is configured to be inserted therein, the mounting hole being provided on a center of the base board body;

a plurality of fixing flow guide plates fixed on the base board body to extend radially outwardly from the mounting hole, the plurality of fixing flow guide plates being arranged on a side of the ceiling and configured to attach the base board body to the ceiling to form the space between the base board body and the ceiling; and a plurality of flow guide plates arranged between two of the fixing flow guide plates, the plurality of flow guide plates being arranged radially outwardly on the base board body from an outer area of an outer circumference of the mounting hole toward an outer edge of the base board body.

2. The cover board according to claim 1, wherein the base board body and the flow guide plates are provided with a photocatalyst, respectively.

3. The cover board according to claim 1, wherein the fixing flow guide plates are arranged to form a cross-shape, and formed to be thicker than the flow guide plates.

4. The cover board according to claim 3, wherein the base board body, the flow guide plates, and the fixing flow guide plates are provided with a photocatalyst, respectively.

5. The cover board according to claim 1, wherein the base board body has a width configured to cover a predetermined area of the ceiling in a width direction thereof so that air is configured to be sucked between the ceiling and the base board body, and to flow downward along wall surfaces of the room.

6. The cover board according to claim 1, wherein the base board body has a width configured to generally cover an entire area of the ceiling.

* * * * *